(12) United States Patent
Tixier

(10) Patent No.: US 9,891,164 B2
(45) Date of Patent: Feb. 13, 2018

(54) HOLMIUM OXIDE GLASSES AS CALIBRATION STANDARDS FOR NEAR INFRARED MOISTURE SENSORS

(71) Applicant: Sebastien Tixier, North Vancouver (CA)

(72) Inventor: Sebastien Tixier, North Vancouver (CA)

(73) Assignee: Honeywell Limited, Mississauga (CA)

( * ) Notice: Subject to any disclaimer, the term of this patent is extended or adjusted under 35 U.S.C. 154(b) by 224 days.

(21) Appl. No.: 14/836,959

(22) Filed: Aug. 27, 2015

(65) Prior Publication Data

US 2017/0059481 A1    Mar. 2, 2017

(51) Int. Cl.
- G01N 21/35 (2014.01)
- G01N 21/3559 (2014.01)
- G01N 21/27 (2006.01)

(52) U.S. Cl.
CPC ....... G01N 21/3559 (2013.01); G01N 21/278 (2013.01)

(58) Field of Classification Search
CPC .......................... G01N 21/3559; G01N 21/278
USPC ...................................................... 250/252.1
See application file for complete search history.

(56) References Cited

U.S. PATENT DOCUMENTS

| | | | |
|---|---|---|---|
| 3,478,210 A | 11/1969 | Janacek | |
| 3,614,450 A | 10/1971 | Hill et al. | |
| 3,641,349 A | 2/1972 | Dahlin | |
| 3,681,595 A | 8/1972 | Dahlin | |
| 3,960,497 A | 6/1976 | Acord | |
| 4,006,358 A | 2/1977 | Howarth | |
| 4,082,950 A | 4/1978 | Chen | |
| 4,306,151 A | 12/1981 | Chase | |
| 4,465,929 A * | 8/1984 | Edgar | G01J 5/52 250/252.1 |
| 4,620,146 A | 10/1986 | Ishikawa et al. | |
| 4,692,616 A | 9/1987 | Hegland et al. | |
| 4,840,706 A * | 6/1989 | Campbell | G01N 21/3554 162/198 |
| 4,928,013 A * | 5/1990 | Howarth | D21F 7/003 250/339.1 |
| 5,235,192 A | 8/1993 | Chase et al. | |
| 5,276,327 A | 1/1994 | Bossen et al. | |
| 6,074,483 A | 6/2000 | Belotserkovsky et al. | |
| 6,078,042 A * | 6/2000 | Fellows | G01N 21/278 250/252.1 |
| 6,281,679 B1 | 8/2001 | King et al. | |
| 7,048,827 B2 | 5/2006 | Watson et al. | |

(Continued)

OTHER PUBLICATIONS

Rand, Practical Spectrophotometric Standards, Clinical Chemistry, vol. 15, No. 9, 1969, p. 839-863.*

*Primary Examiner* — David Porta
*Assistant Examiner* — Gisselle Gutierrez
(74) *Attorney, Agent, or Firm* — Charles H Jew

(57) ABSTRACT

Near infrared moisture sensors using stable holmium oxide glass calibration standards that simulate different moistures levels in paper obviates problems associated with glass encased paper samples. Holmium oxide glass has a strong absorption at 1.93 microns which is close to absorption by paper. Standards can have varying thicknesses to simulate different moisture levels. Didymium glass can also be used with holmium oxide glass. The moisture sensor operates at reference and measurement infrared regions of 1.94 microns and 1.8 microns, respectively.

18 Claims, 2 Drawing Sheets

(56) References Cited

U.S. PATENT DOCUMENTS

| | | |
|---|---|---|
| 7,678,233 B2 | 3/2010 | Beselt |
| 8,660,682 B2 | 2/2014 | Hofman et al. |
| 2003/0114290 A1 | 6/2003 | Landa |
| 2004/0169857 A1* | 9/2004 | Acosta ................. G01N 21/278 356/328 |
| 2005/0119541 A1* | 6/2005 | Lorenz ............... A61B 5/14532 600/316 |
| 2006/0017923 A1* | 1/2006 | Ruchti ...................... G01J 3/28 356/326 |
| 2008/0297796 A1* | 12/2008 | Lukas ....................... G01J 3/28 356/326 |
| 2010/0243876 A1* | 9/2010 | Resch-Genger ..... G01N 21/278 250/252.1 |
| 2016/0064624 A1* | 3/2016 | Yoon .................... H01L 33/504 257/88 |

\* cited by examiner

HOLMIUM OXIDE GLASSES AS CALIBRATION STANDARDS FOR NEAR INFRARED MOISTURE SENSORS

FIELD OF THE INVENTION

The present invention generally relates to sensors and methods for measuring the moisture content in paper products and in particular to on-line infrared moisture sensors that employ holmium oxide glass calibration standards.

BACKGROUND OF THE INVENTION

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Many factors influence the rate at which water is removed which ultimately affects the quality of the paper produced.

It is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process. The on-line sheet property measurements are often accomplished by scanning sensors that periodically traverse the sheet material from edge to edge.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infrared (IR) region. A monitoring or gauge apparatus for this purpose is commonly employed. Such an apparatus conventionally uses either a fixed gauge or a gauge mounted on a scanning head which is repetitively scanned transversely across the web at the exit from the dryer section and/or upon entry to the take up reel, as required by the individual machines. The gauges typically use a broadband infrared source such as a quartz tungsten halogen lamp and two detectors with the wavelengths of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (typically called "reflective" type) in which the source and detector are in a single head on one side of the web, the detector responding to the amount of source radiation scattered from the web. While it is most common to position IR moisture gauges in the more benign dry-end environment, similar gauges are also employed in the wet-end of the papermaking machine. The wet-end moisture gauges are typically located at the end of the press section or the beginning of the dryer section. Gauges in these locations are useful for diagnosis of press and forming sections of the paper machine, or for "setting up" the web for entry into the dryer section.

To ensure that the gauge is stable and accurate over time, a calibration sample or standard is used. The standard is typically a glass encased paper sample that is initially maintained at ambient moisture. The encased paper sample normally exhibits similar characteristics as that of the paper product being measured by the on-line gauge. However, because the glass encased sample has a fixed moisture content it cannot be used to detect a change in the sensitivity of the sensor. An error in the sensor reading can only be corrected by an offset. If not kept properly, the encased sample has a limited lifetime as moisture can leak through the seals between the glass plates.

SUMMARY OF THE INVENTION

The present invention is directed to infrared moisture sensors that employ holmium oxide glass standards instead of glass encased paper samples. The invention is based in part on the recognition that holmium oxide has a strong absorption at 1.93 microns which is close to that of moisture in paper. The glass is very stable and can be made with different levels of holmium oxide in order to simulate different moisture levels in paper. In addition, the thicknesses of the standards can be varied and the glass may incorporate didymium oxide.

In one aspect, the invention is directed to a paper web moisture sensor that includes:

an infrared radiation source disposed to direct a beam of near infrared radiation into the web;

a radiation receiver disposed to detect at least a portion of a beam of radiation emerging from the web, the receiver configured to detect the amount of radiation in first and second separate wavelength regions of the radiation spectrum wherein the first region is positioned around the infrared absorption peak for water and the second region is selected to detect infrared radiation that is insensitive to water and to generate first and second signals therefrom;

computer means operatively coupled to the receiver for computing the amount of water in the web based on the first and second signals; and one or more calibration standards with each standard comprising holmium oxide glass wherein each standard is maneuverable to a calibration position to receive a beam of infrared radiation from the infrared radiation source and to direct a beam of radiation emerging from the standard to the receiver.

In another aspect, the invention is directed to method of standardizing a sensor that measures moisture in paper having a near infrared radiation source and radiation detector with a gap therebetween for directing infrared radiation along a radiation path into the paper and detecting the amount of radiation emerging from the paper, the detector being configured to detect the amount of radiation in first and second separate wavelength regions of the radiation spectrum wherein the first region is positioned around the infrared absorption peak for water and the second region is selected to detect infrared radiation that is insensitive to water and to generate first and second signals therefrom and means operatively coupled to the detector for computing the amount of water in the paper based on the first and second signals, said method including the steps of:

employing a standard that simulates a predetermined moisture level wherein the standard comprises holmium oxide glass;

positioning the standard into the radiation path;

measuring the radiation in the first wavelength region that emerges from the paper;

measuring the radiation in the second wavelength region that emerges from the paper; and standardizing the detector and/or the sensor.

DETAILED DESCRIPTION OF PREFERRED EMBODIMENTS

Figure 1:
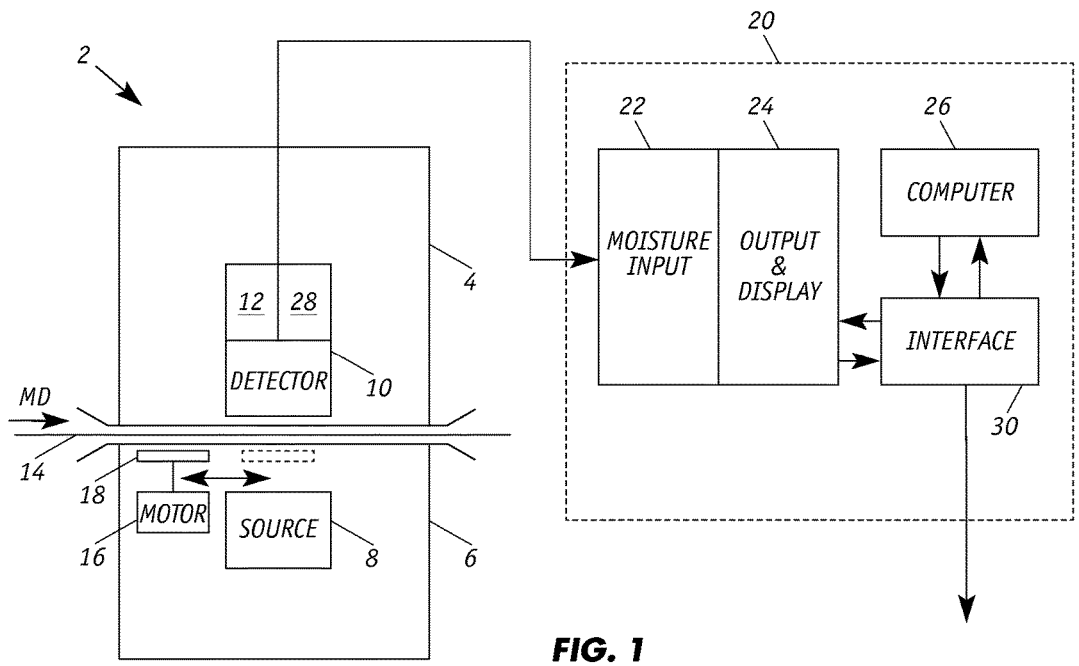
FIG. 1 illustrates an on-line two-channel moisture sensor operating in the transmission mode.

FIG. 1 illustrates a non-contacting optical sensor 2 that includes enclosures 4 and 6 (each also called a "scanner head" or "head") that house sensor components for measuring moisture in paper web 14 which is traveling in the machine direction (MD). Scanner 2 includes a radiation or light source 8 that is positioned in head 6 and a radiation receiver or detector 10 that is positioned in head 4. The upper and lower scanner heads 4, 6 are aligned. In operation of sensor 2, a lens in light source 8 focuses incident radiation through an aperture toward moving web 14 and a lens in detector 10 collects radiation that is transmitted through the web. Movement of the upper and lower scanner heads 4, 6 in the cross direction, which is traverse to the MD, is coordinated so that light is detected by detector 10 with channels 12 and 28. The signals generated by radiation detector 10 are directed to a moisture level input unit 22. The moisture level unit is part of an overall digital process unit 20 which, along with an interface unit 30 and a computer 26, processes the information from scanner head 4 to provide an input at unit 24 of the actual moisture level of the web. Interface unit 30 has an output which may be used to control actual parameters of the paper machine or sheet material. Light source 8 can comprise, for instance, a Quartz Tungsten Halogen lamp to irradiate material 14 with radiation having wavelengths in at least first and second separate wavelength regions of the electromagnetic spectrum that are referred to as reference and measurement wavelength bands.

In particular, the reference wavelength band is chosen such that it lies outside an electromagnetic absorption band or region of the spectrum of strong absorption by the water in the paper web, that is, where there is relatively little absorption by water. Typically, this is at about 1.8 microns. In the reference region of the spectrum, most of the infrared absorption is due to paper fibers themselves and not to the moisture in the web. The measurement wavelength band is chosen such that it lies within an electromagnetic absorption band of water. Typically, this is at about 1.94 microns. Analysis of the infrared radiation detected at the reference and measurement wavelength regions yields the moisture level of the paper. Preferably, moisture level can be inferred from the ratio of the absorption at the two regions.

As further shown in FIG. 1, a standard 18, which is connected to motor 16, can be selectively interposed in the radiation path between source 8 and detector 10. The standard can be pivoted for rotation on a shaft which is driven through a universal joint by a rotary solenoid unit. The standard is made of calibration material, which is typically configured as a disc, and which is made of holmium oxide glass. Instead of employing a mechanized device to automatically manipulate standard 18, the process can be implemented manually given that sensor verification is required only infrequently.

Holmium oxide glass is a glass composition that is typically made by adding holmium oxide ($Ho_2O_3$) to a silica-based glass composition and then processing the mixture with conventional glass melting and refining techniques. The holmium oxide levels in the mixture can be varied to achieve the desired levels of adsorption by the holmium oxide glass. In addition, didymium oxide which exhibit similar adsorption characteristics at 1.93 microns can be added with the holmium oxide in the mixture.

Figure 2:
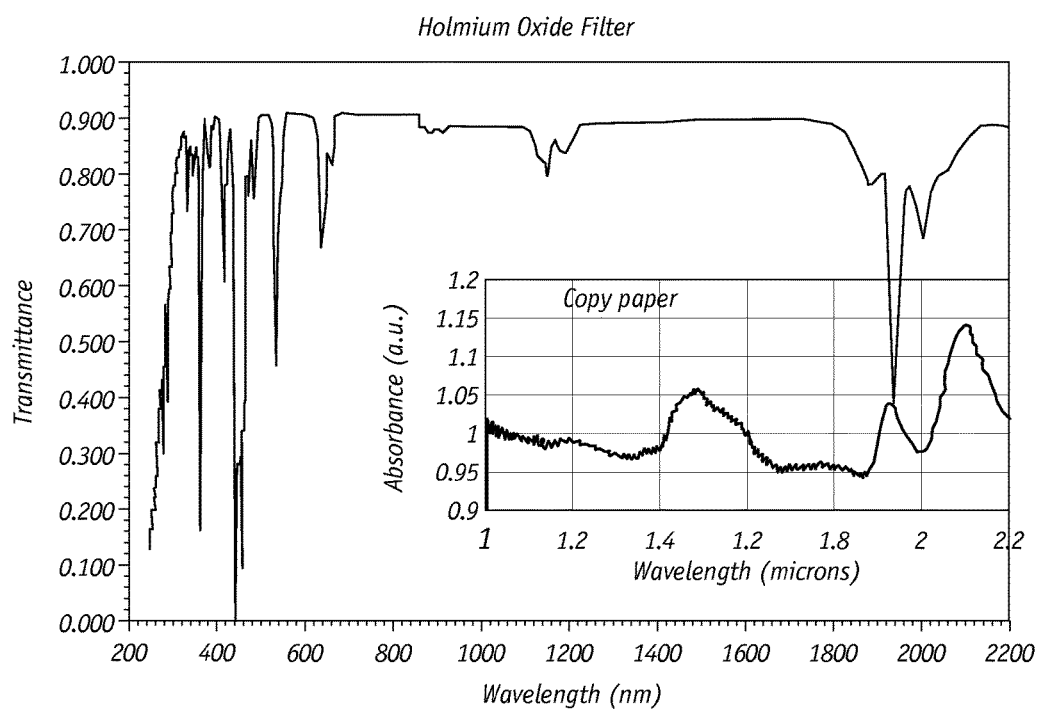
FIG. 2 is the spectrum of holmium oxide glass together with a near infrared spectrum of copy paper.

FIG. 2 is the spectrum of holmium oxide glass, that is commercially available from HOYA Corporation USA (Santa Clara, Calif.) as product HY-1, which exhibits an absorption peak at around 1.9 microns which is similar to that of copy grade paper. Didymium oxide has a similar absorption peak in the vicinity of 1.93 microns. Standards of the present invention can also include calibration materials that comprise individual layers of holmium oxide glass and didymium glass that are stacked together.

Typically, after sensor 2 of FIG. 1 has been assembled at the factory, it is first calibrated by establishing "reference" values through sensor moisture measurements where no sample is present in the gap between the radiation source 8 and detector 10. Next, the sensor is calibrated empirically by positioning successive actual paper samples with known moisture levels into the gap. A calibration curve, look-up table, and/or mathematic model (collectively referred as "calibration data") that express the calculated paper moisture level as a function of measured radiation by the detector is generated and stored in the computer memory. When sensor 2 is installed at a papermaking facility, it is ready for use by the customer.

Standard 18 of FIG. 1 allows for on-line recalibration. The stable calibration material is constructed to simulate paper having a known moisture level. This can be achieved by tailoring the thickness of the calibration material to exhibit the desired simulated moisture level and/or by incorporating different amounts of holmium oxide in the glass. Indeed, sensor 2 can be equipped with a plurality of standards 18 with different thicknesses (or holmium oxide glass contents) so as to permit recalibration through a range of simulated moisture levels.

With the present invention, standardization or recalibration of detector 10 of sensor 2 can be based on readings from detector 10 taken with and without the inventive holmium oxide glass standards in the gap. Within this protocol, detector readings from both the first and second wavelength regions (and other wavelength regions if desired) are analyzed using a conventional algorithm that is stored in computer 26. The goal of this standardization is to insure that the detector is generating correct signals. In the case where no standard material is in the gap, the detector may be allowed to drift around the "reference" values. Changes in the ratio of the reference values to the signal values measured with the standard in the gap are employed to recalibrate the sensor. Thus, it is not necessary to manipulate the sensor to read the correct "reference" values.

With the present invention, in another recalibration protocol, the sensor itself can be similarly recalibrated to generate the appropriate sensor correction factor, where necessary, so that the sensor yields the corrected calculated moisture or water weight measurements.

Figure 3:
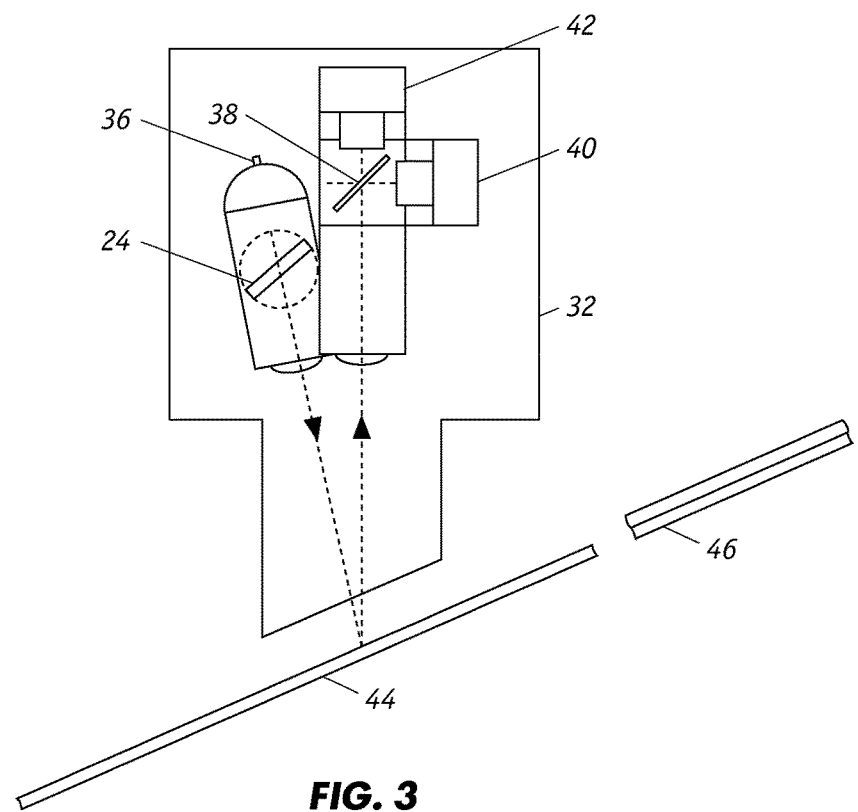
FIG. 3 illustrates a two channel moisture sensor operating in the reflection mode.

FIG. 3 depicts a reflectance-type sensor for measuring the amount of the moisture in water in paper sheet 44. The sensor includes detector assembly 32 that comprises a tungsten-halogen source 36 of continuous wave radiation in the infrared region and a detector assembly of two infrared detectors that are housed in a temperature-controlled enclosure. The broad-band infrared source energy 36 is directed at the sheet 44 at an angle that minimizes sensitivity to sheet flutter and surface characteristics. The diffused reflection mode is preferred. The angle typically ranges from about 10 to about 25 degrees from normal. The detector assembly comprises a moisture sensor that includes moisture measurement filter/detector 42 and moisture reference filter/detector 40. As is apparent, the sensor can be structured to include additional measurement and reference filter/detectors to detect the presence of other infrared radiation sensitive materials that may be in the paper. For example, a four-channel sensor or six-channel sensor can measure one and two other components, respectively, in addition to moisture. The energy reflected from the sheet is wavelength-analyzed by passing the beam through the beam splitters 38 and the appropriate filters to the individual detectors. The detector assembly further includes a conventional infrared energy modulator 60 which comprises, for example, a rotating light chopper, for example, which provides a high level of infrared energy modulation. The output of each of the detectors (both measure and reference) is transmitted to the digital process unit (not shown) for analysis.

The sensor of FIG. 3 is equipped with standard 46 for calibration. As shown, the calibration material comprises a two layered stack with each layer comprising holmium oxide glass discs or wherein one of the layers is didymium glass. A plurality of such stacks which stimulate different moisture levels in paper can be maneuvered into the location where paper sheet 44 normally occupies for recalibration. When standard 46 is used in a reflection type sensor, the standard can incorporate a reflective layer, such as an aluminized KAPTON layer, on the lower back surface of the standard.

Figure 4:
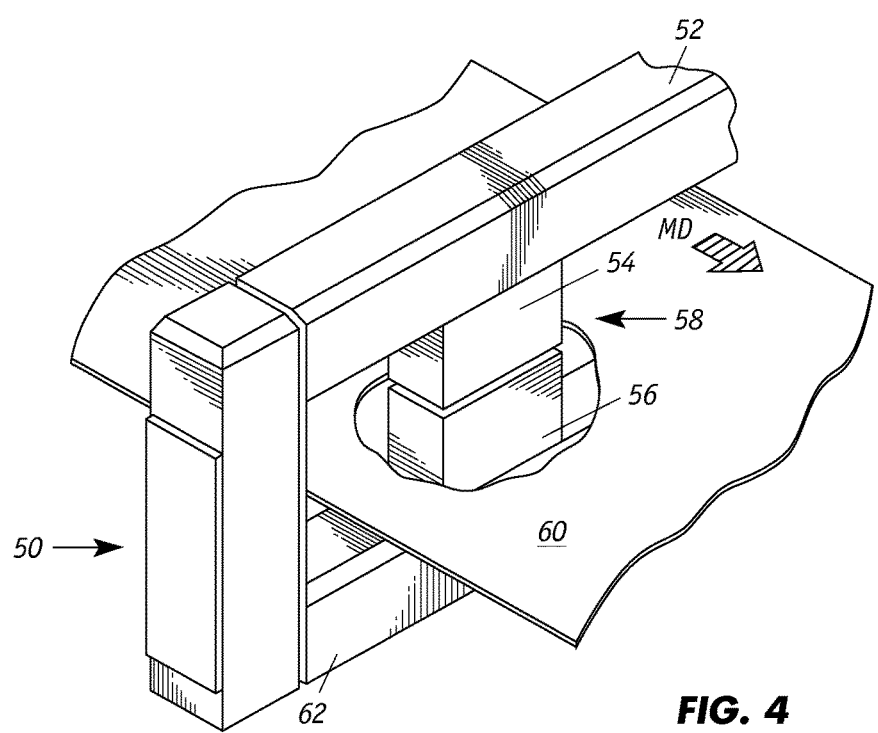
FIG. 4 illustrates a sheetmaking system incorporating the moisture sensor.

The FIG. 4 illustrates one particular implementation of the sensor that is shown in FIG. 1. In particular, the radiation source and detector are housed in a dual head scanner 58 of scanner system 50 which can be employed to measure the water weight or moisture content in paper. Upper scanner head 54 moves repeatedly back and forth in the CD across the width of the moving sheet 60, which moves in the MD, so that the characteristics of the entire sheet may be measured. Scanner 58 is supported by two transverse beams 52, 62 on which are mounted upper and lower scanning heads 54, 56. The operative faces of the lower and upper scanner heads 56, 54 define a measurement gap or window that accommodates sheet 60. The lower scanner head 56 may include a sheet stabilization system such as an air-bearing stabilizer (not shown) to maintain the sheet on a consistent plane as it passes through the measurement window. The movement of the dual scanner heads 54, 56, is synchronized with respect to speed and direction so that they are aligned with each other.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A paper web moisture sensor comprising:
   an infrared radiation source disposed to direct a beam of infrared radiation into the web;
   a radiation receiver disposed to detect at least a portion of a beam of radiation emerging from the web, the receiver configured to detect the amount of radiation in first and second separate wavelength regions of the radiation spectrum wherein the first region is positioned around the infrared absorption peak for water, which is about 1.94 microns, and the second region is selected to detect infrared radiation that is insensitive to water, which is about 1.8 microns, and to generate first and second signals therefrom;
   computer means operatively coupled to the receiver for computing the amount of water in the web based on the first and second signals; and
   one or more calibration standards with each standard comprising holmium oxide glass wherein each standard is maneuverable to a calibration position to receive a beam of infrared radiation from the infrared radiation source and to direct a beam of radiation emerging from the standard to the receiver which measures the radiation in the first wavelength region and the radiation in the second wavelength region to standardize the sensor.

2. The sensor of claim 1 wherein the one or more calibration standards comprises holmium oxide glass and didymium glass.

3. The sensor of claim 1 wherein each of the one or more calibration standards consists essentially of holmium oxide glass.

4. The sensor of claim 1 comprising a plurality of calibration standards exhibiting different degrees of infrared radiation absorption.

5. The sensor of claim 4 comprising a plurality of calibration standards with different levels of holmium oxide therein.

6. The sensor of claim 4 comprising a plurality of calibration standards having different thicknesses.

7. The sensor of claim 4 wherein the different degrees of infrared radiation absorption correspond to different predetermined levels of moisture absorption.

8. The sensor of claim 4 wherein the plurality of calibration standards comprise a plurality of calibration standards each consisting essentially of holmium oxide glass.

9. The sensor of claim 1 comprising means for constructing a calibration curve from which a correction factor can be obtained and applied to calculate paper web water weight or moisture to generate corrected water weight or moisture.

10. The sensor of claim 1 wherein the sensor operates in the transmission mode with the receiver being configured to detect radiation that has been transmitted through the paper web.

11. The sensor of claim 1 wherein the sensor operates in the reflection mode with the receiver being configured to detect radiation that has been reflected from the paper web.

12. A method of standardizing a sensor that measures moisture in paper having an infrared radiation source and radiation detector with a gap therebetween for directing infrared radiation along a radiation path into the paper and detecting the amount of radiation emerging from the paper, the detector being configured to detect the amount of radiation in first and second separate wavelength regions of the radiation spectrum wherein the first region is positioned around the infrared absorption peak forwater, which is about 1.94 microns, and the second region is selected to detect infrared radiation that is insensitive to water, which is about 1.8 microns, and to generate first and second signals therefrom and means operatively coupled to the detector for computing the amount of water in the paper based on the first and second signals, said method comprising:
(a) employing a standard that simulates a predetermined moisture level wherein the standard comprises holmium oxide glass;
(b) positioning the standard into the radiation path;
(c) measuring the radiation in the first wavelength region that emerges from the paper;
(d) measuring the radiation in the second wavelength region that emerges from the paper; and
(e) standardizing the detector and/or sensor.

13. The method of claim 12 wherein the radiation is either transmitted through or reflected from the paper.

14. The method of claim 12 where step (e) comprises standardizing the detector to yield a correction factor to modify detector measurements.

15. The method of claim 12 wherein step (e) comprises standardizing the sensor to yield a correction factor to modify sensor moisture or water weight calculations.

16. The method of claim 12 comprising repeating steps (b), (c), and (d) a plurality of times using standards exhibiting different degrees of infrared radiation absorption before executing step (e).

17. The method of claim 16 wherein the standards exhibiting different degrees of infrared radiation absorption have different levels of holmium oxide therein.

18. The method of claim 16 wherein the standards exhibiting different degrees of infrared radiation absorption have different thicknesses.

* * * * *